United States Patent [19]

Chang et al.

[11] Patent Number: 4,790,928

[45] Date of Patent: Dec. 13, 1988

[54] CATALYTIC CONVERSION OVER DEHYDROXYLATED ZEOLITE

[75] Inventors: Clarence D. Chang, Princeton; Nai Y. Chen, Titusville; Stuart D. Hellring, Trenton, all of N.J.; Ying-Yen P. Tsao, Lahaska; Dennis E. Walsh, Richboro, both of Pa.

[73] Assignee: Mobile Oil Corporation, New York, N.Y.

[21] Appl. No.: 153,395

[22] Filed: Feb. 8, 1988

Related U.S. Application Data

[63] Continuation-in-part of Ser. No. 944,629, Dec. 19, 1986, Pat. No. 4,724,270, which is a continuation-in-part of Ser. No. 783,269, Oct. 4, 1985, abandoned, which is a continuation of Ser. No. 603,049, Apr. 23, 1984, abandoned.

[51] Int. Cl.[4] .................... C10G 47/02; C10G 11/02; C07C 5/13
[52] U.S. Cl. .................................. 208/111; 208/120; 208/124; 585/739
[58] Field of Search ................ 585/739; 208/120, 124, 208/111

[56] References Cited

U.S. PATENT DOCUMENTS

| | | | |
|---|---|---|---|
| 3,097,115 | 7/1963 | Moos | 136/120 |
| 3,939,058 | 2/1976 | Plank | 208/120 |
| 4,016,218 | 5/1977 | Haag et al. | 260/671 |
| 4,060,568 | 11/1977 | Rodewald | 260/682 |
| 4,141,859 | 2/1979 | Plank | 208/139 |
| 4,276,438 | 6/1981 | Chu | 585/467 |
| 4,430,200 | 2/1984 | Shibabi | 502/60 |
| 4,661,467 | 4/1987 | Kuehl | 502/63 |

OTHER PUBLICATIONS

Breck, D. W., Zeolite Molecular Sieves, pp. 493–495.

*Primary Examiner*—Curtis R. Davis
*Attorney, Agent, or Firm*—Alexander J. McKilloo; Michael G. Gilman; Malcolm D. Keen

[57] ABSTRACT

The acidity of a zeolite catalyst is reduced by calcination in an essentially water-free atmosphere at temperatures above 700° C., preferably from 725° to 800° C., to reduce the alpha value to less than about 10 percent of its original value. The low acidity catalysts produced in this way may be used for conversions requiring low acidity, shape selective catalysis, including dewaxing. The calcined, low acidity catalysts exhibit improved dewaxing activity.

20 Claims, 1 Drawing Sheet

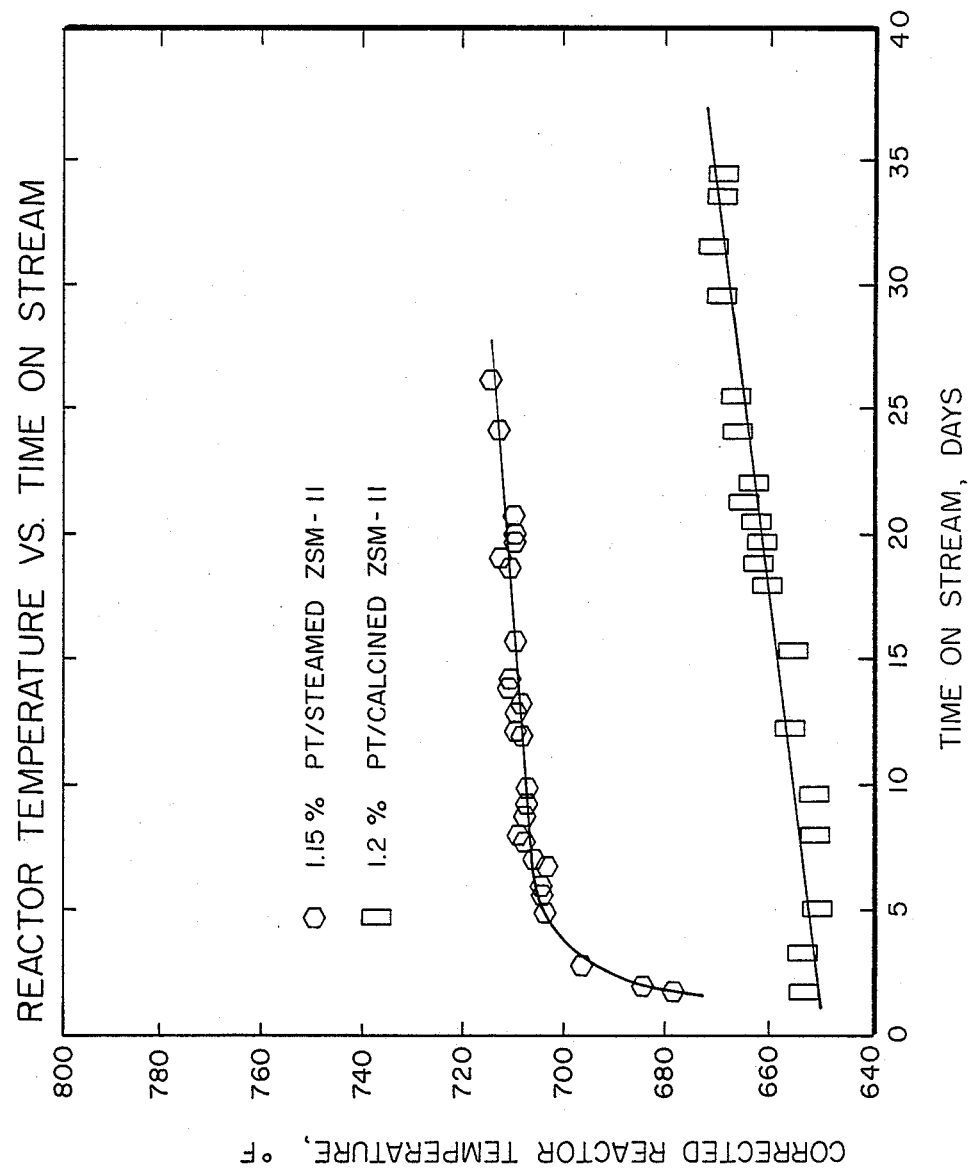

CATALYTIC CONVERSION OVER DEHYDROXYLATED ZEOLITE

CROSS REFERENCE TO RELATED APPLICATIONS

This application is a continuation-in-part of our copending patent application Ser. No. 944,629, now U.S. Pat. No. 4,724,270, filed Dec. 19, 1986 which was, in turn, a continuation-in-part of Ser. No. 783,269, filed Oct. 4, 1985, and now abandoned, which was a continuation (FWC) of Ser. No. 603,049, filed Apr. 23, 1984, and now abandoned. The disclosures of those applications are incorporated in the present application by this reference to them.

FIELD OF THE INVENTION

This invention relates to a process for preparing low acidity zeolites and the use of such zeolites in catalytic conversions, especially in dewaxing processes.

BACKGROUND OF THE INVENTION

Zeolitic materials, both natural and synthetic, are known to have the capability for catalyzing various types of hydrocarbon conversion reactions which take place in the presence of catalytic sites with acidic functionality. These zeolite materials generally have ordered, porous crystalline structures within which there are a number of small cavities that are interconnected by a number of still smaller channels. These cavities and channels are precisely uniform in size within a specific zeolitic material. Since the dimension of these pores are such as to accept for adsorption purposes molecules of certain dimensions, while rejecting those of larger dimension, these materials have commonly been known to be "molecular sieves" and are utilized in a variety of ways to take advantage of the adsorptive propertis of these compositions. The structures may be determined by X-ray diffraction techniques.

These molecular sieves include a wide variety of positive ion-containing crystalline aluminosilicates and other siliceous materials such as borosilicates, ferrosilicates and gallosilicates in which the presence of the trivalent metal at sites within the silicate structure provides the desired acidic functionality in an environment which permits access to the site only by molecules of appropriate size so that the acid catalyzed reactions are carried out in a "shape selective" manner. Metal cations such as sodium which are usually present in these materials when they are synthesized may be converted to the hydrogen form by exchange with ammonium ions followed by heating to drive off ammonia or by direct exchange with an acid such as hydrochloric acid, if the zeolite is not degraded by the acid. Useful catalysts are also produced by a combination of ion-exchange treatments in which the crystalline silicate may be converted to the acid form and they may be ion exchanged with a solution of various metal salts to produce the metal exchanged zeolite.

The acid activity of aluminosilicate zeolites may be so high that conventional hydrocarbon conversion processes and apparatus cannot take full advantage of this high activity. For example, in catalytic cracking, high activity may yield excessive coke formation and the production of large amounts of light gases. The acid activity of zeolite catalysts may, however, be lowered to a level at which the use of such catalysts in catalytic conversions is satisfactory and, in fact, results in a considerable increase in the efficiency of such processes. Reactions which have been performed successfully over low acidity zeolites include the conversion of oxygenates such as methanol and dimethyl ether to olefin and other hydrocarbon products, xylene isomerization, aromatic alkylation, and olefin oligomerization, as well as catalytic dewaxing and hydrodewaxing and hydroisomerization.

One method of reducing the activity of aluminosilicate zeolite catalyst is by compositing the zeolite with a matrix material which is relatively inactive. Suitable matrix materials include inorganic oxides, such as those of silica, zirconia, alumina, magnesia and combinations of such materials with one another, as well as clays and other refractory materials.

Other methods to reduce the activity of acid zeolites include cation exchange with sodium or other alkali metal cations or by forming the zeolites with high silica:alumina mole ratios in the structure or framework. An important method in reducing the activity of zeolite catalysts is by a process of steam treating. By controlled steaming, it is possible to produce zeolite catalysts having any desired degree of activity. The degree of steaming of a specified catalyst to achieve a desired activity level is largely dependent upon the nature of the zeolite. Steam treatment, however, often requires long periods of time to treat the catalyst effectively for activity reduction.

U.S. Pat. No. 3,939,058 discloses methods of modifying the catalytic properties of zeolite cracking catalysts. One such method is calcination which is defined as heating at high temperatures but below the sintering temperature of the zeolite for varying periods of time. Other methods are also disclosed, including compositing the zeolite in a matrix and steam treatment. The patent further discloses that the crystallinity retention of catalysts may be improved by precalcination of the crystalline aluminosilicate. For example, the patent states that it has been found possible to preserve the crystallinity of aluminosilicates such as the rare earth exchange synthetic faujasites, by calcining the zeolite to drive off water, thus forming a more suitable structure and minimizing loss in crystallinity during subsequent rapid drying, as in spray drying, wet processing, steaming and aging. The calcining may be accomplished by heating the crystalline aluminosilicate sieve after ion exchange to a temperature below the sintering temperature of the sieve and generally in the range of from 500° to 1600° F. (about 260° to 870° C.).

Similarly, U.S. Pat. No. 4,141,859 discloses a method of controlling the relative acid activity of zeolite catalysts, by treating the zeolitic component with air or steam at elevated temperatures, e.g., up to 1700° F. (about 925° C.) in air or at temperatures from about 800° F. to about 1700° F. (about 425° C. to 925° C.) in steam.

Calcination of the freshly synthesized zeolite to remove adsorbed water and organic materials that have been used to form the zeolite crystals is necessary to activate the zeolite and accordingly has generally been employed. Also, as stated above, precalcination of the zeolite has been found to stabilize the crystallinity of the zeolite. However, heat treatment may remove hydroxyl groups from the framework of the zeolite. Thus, dehydroxylation of a decationized Y zeolite is discussed in *Zeolite Chemistry and Catalysts,* ACS Monograph 171, pages 142 and 143, in which dehydroxylation of Y zeolite is stated to result from prolonged calcination at relatively high temperatures, resulting finally in the structural collapse of the zeolite and the formation of an amorphous silica or silica-alumina structure. For these reasons, the use of high temperatures has generally been avoided in zeolite synthesis. When organic materials are to be removed from the freshly synthesized zeolite, temperatures of about 1000° F. (about 540° C.) are typical and generally not exceeded in order to avoid damage to the crystal structure.

Calcination or high temperature treatment has been employed in various catalyst treatments to achieve particular results, for example, to convert impregnated metal or other compounds to different forms as described in U.S. Pat. Nos. 4,276,438 and 4,060,568 or to destroy ion exchange capacity as described in U.S. Pat. No. 3,097,115. However, even in such cases the use of higher temperatures, e.g. above 500° C., has not been preferred because of the undesirable effect on the structure of the zeolite.

SUMMARY OF THE INVENTION

In accordance with the present invention, the acid activity (as typically measured by the alpha scale) of intermediate pore size zeolites such as ZSM-5 can be reduced by calcining the zeolites in the absence of water at temperatures greater than about 600° C. but less than the temperature at which the crystallinity of the zeolite collapses. It has been found that the alpha activity of these zeolites can be reduced to less than 10% of the initial alpha value by the high temperature treatment. The resultant low acidity catalysts can be used effectively in catalytic conversions in which such low acidity zeolite catalysts are effective to catalyse the conversion reaction. The high temperature treatment to reduce the alpha activity of the present invention takes less time and may yield a more stable catalyst than steam deactivation.

With certain reactions improved selectivity to the desired products may be noted. This is particularly the case with the conversion of oxygenates to hydrocarbons, for example, as disclosed in Ser. No. 944,629, now U.S. Pat. No. 4,724,270, to which reference is made for details of such processes.

Other reactions where improved selectivities to desired products are noted include the isomerization of alkylaromatic compounds such as xylenes (where improved selectivity to the para-isomer is noted), olefin oligomerisation, catalytic dewaxing and hydrodewaxing (where improved selectivity of removal of straight and slightly branched chain paraffins may be secured) and paraffin hydroisomerisation.

In accordance with the present invention, the zeolites which have been subjected to high temperature calcination are used for catalytically dewaxing hydrocarbon feedstocks. It has been found that the zeolites which have been subjected to the high temperature calcination (HTC) treatment are more active for dewaxing than similar zeolites which have been treated by steaming. The calcined zeolites will produce a product of a given pour point at a lower dewaxing temperature than the steamed zeolites, permitting dewaxing cycles to be extended.

DETAILED DESCRIPTION

In accordance with the present invention, the alpha activity of a dewaxing catalyst comprising a crystalline aluminosilicate zeolite having a silica-to-alumina ratio of a least about 12 and a Constraint Index within the approximate range of 1 to 12 can be reduced by heat treating the zeolite at temperatures of 600° C. and above, preferably above 700° C. Non-limiting examples of crystalline aluminosilicate zeolites that can be effectively treated in accordance with this invention include ZSM-5, ZSM-11, ZSM-12, ZSM-23, ZSM-35, ZSM-38 and ZSM-48.

The synthesis and characteristics of zeolite ZSM-5 are described in U.S. Pat. No. 3,702,886; of zeolite ZSM-11 in U.S. Pat. No. 3,709,979; of zeolite ZSM-12 in U.S. Pat. No. 3,832,449; of zeolite ZSM-23 in U.S. Pat. No. 4,076,842; of zeolite ZSM-35 in U.S. Pat. No. 4,016,245; of zeolite ZSM-38 in U.S. Pat. No. 4,406,850 and of zeolite ZSM-48 in U.S. Pat. No. 4,397,827.

These above-defined zeolites can function as catalysts even when modified to have low alpha values, typically less than 10, and even at alpha values substantially lower than 1. As noted above, low acid activity has previously been achieved by using zeolites of very high silica/alumina ratio, extensive ion exchange of the zeolite with sodium or other alkali metal cations, or by severe temperature steaming of zeolites.

In accordance with the present invention, the alpha activity of the above-defined zeolites is reduced by calcining the zeolites at high temperatures, above 600° C., preferably above 700° C., in an essentially water-free atmosphere (although minor, non deleterious amounts of water may be present).

Alpha activity is an approximate indication of the catalytic cracking activity of the catalyst compared to a standard catalyst. Alpha is the relative rate constant (rate of n-hexane conversion per unit volume of oxides, compositions per unit time). It is based on the activity of highly active silica-alumina cracking catalyst taken as alpha=1 (12.5% cracking at 5 minutes on stream) at a temperature of 538° C. Alpha activity is further described in U.S. Pat. No. 3,354,078 and the *Journal of Catalysis*, Vol. 4, pages 522–529, August, 1965. See also *J. Catalysis* 61, 395 (1980). The Constraint Index of a zeolite may be determined by the method described in U.S. Pat. No. 4,016,218.

Generally, ZSM-5 and other intermediate pore size zeolites having a Constraint Index of 1–12 are activated by calcining the zeolite at temperatures of about 550° C. to remove water and organic directing agents which are typically included in the synthesis mixture from which the zeolite is made. In accordance with present invention, however, the zeolites are treated above 600° C. and preferably at temperatures from 700° to 800° C. (but less than the sintering temperature of the zeolite) to reduce the acid activity of the zeolite. Significant dehydroxylation does not commence at least until 700° C. or higher temperatures. The temperature should therefore be above 700° C., preferably above 725° C. although normally temperatures above 800° C. will not be preferred both for reasons of convenience (special high temperatures equipment will be needed at higher temperatures) and because dehydroxylation has been found to occur most rapidly in the range between 700° and 800° C. Although the temperature required for reducing the alpha activity may vary between the individual zeolites the treatment temperature should generally not exceed 1100° C., above which temperature the structural framework begins to collapse.

Calcination is achieved by heating the zeolite at the desired elevated temperature, in dry air, hydrogen or an inert gas such as nitrogen. Typically, the heat treatment proceeds for at least 1 hour, although heating may last between 1–24 hours. The heat treatment is dry (no water), although up to 2% by weight steam may be included in the calcining atmosphere.

It is theorized that at the high temperature used for achieving reduced alpha activity, removal of framework hydroxyl groups is taking place (i.e. dehydroxylation). The heat treatment should not continue beyond the point at which crystallinity of the zeolite is lost. Typically, at least 55% of the crystallinity of the zeolite will be maintained under the heat treatment conditions. However, catalytic activity and selectivity to desired products may be enhanced in spite of the decrease in acid activity, as measured by the alpha value.

The final alpha value of the zeolite is typically below 100 and in many cases below 50. Alpha values even lower than this may nonetheless be possessed by catalytically useful materials in reactions requiring only a limited degree of acidity.

The reactions which may be catalysed by the zeolites treated in this way are those in which a feed is subjected to an acid-catalysed conversion by means of the solid, zeolite catalyst. The acidic sites at which the catalytic reaction mechanisms take place are found within the porous internal structure of the zeolite where access to these sites may be gained by the reactants. The porous structure of the zeolite may also impede egress by the reaction products and therefore it is necessary, if the reaction is to occur, that the reaction products should also be able to leave the pore structure of the zeolite after the catalytic mechanisms have taken place.

The calcined zeolite is used for catalytically dewaxing petroleum fractions containing waxy components, principally straight chain paraffins and slightly branched chain paraffins e.g. mono-methyl paraffins. Feeds containing such components may be either wide boiling range feeds such as crudes, reduced crudes or atmospheric tower resids or limited boiling range feeds such as vacuum gas oils, deasphalted and solvent-extracted residua, middle distillates such as kerosene or jet fuel and lubricant fractions typically boiling above 400° F. (about 205° C.). Middle distillates will typically boil in the range 330°–700° F. (165°–370° C.) more commonly 330°–650° F. (165°–345° C.). Gas oils will typically boil above about 600° F. (about 315° C.), usually from 650°–1050° F. (about 345°–565° C.).

The dewaxing is carried out by contacting the feed with the zeolite dewaxing catalyst at an elevated temperature, usually in the presence of hydrogen. Hydrogen is not consumed for zeolites which do not contain a metal function as the dewaxing reaction proceeds by shape-selective cracking of the waxy components. Nevertheless, its use extends catalyst cycle life by reducing aging. For catalysts containing noble metals, hydrogen consumptions are low (typically not more than 400 SCF/Bbl) and its use may facilitate the dewaxing reaction itself. The process is normally operated in a fixed, trickle-bed reactor in a downflow mode.

Dewaxing conditions are typically of elevated temperature and pressure. The temperature is conventionally raised during the course of each dewaxing cycle to compensate for catalyst aging so as to achieve the desired product pour point. Typical start-of-cycle (SOC) temperatures are about 400°–550° F. (about 260°–290° C.). The dewaxing cycle is continued until end-of-cycle (EOC) temperature is reached, typically at about 670°–750° F. (about 355°–370° C.), especially with lube product as thermal and oxidative stability decreases markedly at higher temperatures. Pressures of 400 psig (2860 kPa abs.) or more are typical, usually 400–2000 psig (2860–13890 kPa abs.), usually depending on the equipment available. Space velocity is typically 0.1–10 hr$^{-1}$ (LHSV), more commonly 0.5–2.0 LHSV. Hydrogen circulation rates of 1000–4000 SCF/Bbl (about 180–720 n.l.l.$^{-1}$) are typical.

The zeolite may be matrixed with a binder such as silica, alumina or silica-alumina in order to improve mechanical strength as well as to modify catalyst activity by the use of the essentially inactive binder.

The catalyst may also contain a metal component with hydrogenative-dehydrogenation activity in order to facilitate catalyst reactivation with hydrogen after completion of a dewaxing cycle. Metals or Group VIIIA (IUPAC Periodic Table) are useful for this purpose, including nickel, cobalt or noble metals such as palladium or platinum. Metals of other groups having hydrogenation activity are also useful, especially when combined with a Group VIIIA metals, e.g. molybdenum or tungsten. Typically up to about 10 weight percent metal is sufficient, usually about 0.5–5 weight percent.

When the catalyst contains no metal function, or only a relatively weak hydrogenation/dehydrogenation function such as nickel, the dewaxing products will contain substantial amounts of olefinic components produced by the shape-selective cracking reactions. Therefore, it may be desirable, especially in the case of lubricant products, to hydrotreat the dewaxed fraction in order to saturate olefins boiling in the product boiling range.

Correctional hydrotreating catalysts may be used for this purpose e.g. cobalt-molybdenum, nickel-molybdenum or silica, alumina or silica-alumina or another substantially inert, porous support.

The following Examples illustrate the invention. All samples of the thermally deactivated ZSM-5 produced in Examples 1–4 originated from the NH$_4$ form ZSM-5 (SiO$_2$/Al$_2$O$_3$=70), which had been converted into the proton(H)-form by calcination 1° C./min. to 538° C., then held 10 hr., alpha=214.

EXAMPLE 1

An HZSM-5 sample was calcined at 800° C. for 1 hour, then at 1000° C. for 1 hour to a final alpha value of 0.4).

EXAMPLE 2

An HZSM-5 sample was calcined at 1000° C. for 1 hour, to a final alpha value of 0.9).

EXAMPLE 3

An HZSM-5 sample was calcined at 800° C. for 1 hour, (alpha=12).

EXAMPLE 4

An HZSM-5 sample, as a mixture (65%) in Al$_2$O$_3$, was calcined at 1038° C. for 16 hours (alpha=0.1).

EXAMPLE 5

An alumina-bound ZSM-11 extrudate (65 wt. pct. zeolite, alpha=97 based on extrudate) was calcined in dry air at 800° C. for 16 hours to a final alpha value of 7 for the extrudate. It was then treated with hot 1M aqueous ammonium nitrate solution (approx. 50/1 wt./wt., 5 hours, 90° C., 37 alpha post NH$_4$NO$_3$ treatment) and platinum exchanged at room temperature using a 0.8 weight percent solution of platinum tetraamine nitrate (approximately 8/1 wt./wt., 24 hours). The platinum content of the air calcined final catalyst was 1.2 wt. percent.

The high temperature calcined (HTC) catalyst was tested for gas oil dewaxing together with a comparison catalyst which had been produced by steaming an alumina-bound ZSM-11 extrudate (65 wt. pct. zeolite) to a final alpha value of 20 based on the extrudate, followed treatment with hot 1 m aqueous $NH_4NO_3$, and then by platinum exchange and air calcination at 350° C. to give a final platinum content of 1.15 weight percent.

The catalysts were used for dewaxing South East Asian vacuum gas oil. Two such oils were used, of similar composition. VGO-1 was used for about one week from SOC after which VGO-2 was used for the remainder of the cycle. Oil compositions are given in Table 1 below.

TABLE 1

| Properties of Vacuum Gas Oils | | |
|---|---|---|
| | VGO-1 | VGO-2 |
| H/C, atomic | 1.93 | 1.90 |
| S, wt. % | 0.1 | 0.078 |
| N, ppm | 340 | 350 |
| Basic N, ppm | 127 | 121 |
| Ni, ppm | 0.1 | 0.2 |
| V, ppm | not detected | 0.3 (less than) |
| Br No. | 2.9 | — |
| CCR, wt. % | 0.05 (less than) | 0.12 |
| Pour Point, °F. | 115 | 115 |
| 650° F.−, wt. % | 7.4 | 4.0 |
| 650° F.+, wt. % | 92.6 | 96.0 |
| Paraffins, wt. % | 54.8 | 62.6 |
| Naphthenes, wt. % | 27.0 | 17.1 |
| Aromatics, wt. % | 18.2 | 20.3 |

Both catalysts were pre-sulfided before use with 2% $H_2S/H_2$. Dewaxing was carried out at 400 psig (2860 kPa abs.) and 2500 SCF/Bbl (445 n.l.l.$^{-1}$)$H_2$ circulation. Space velocity was matched for WHSV since the density of the HTC catalyst was slightly less than that of the steamed catalyst at 1.45 WHSV. The gas oil was dewaxed to a target pour point of 50° F. (10° C.) for the 330° F.+ (165° C.+) product, except as shown below. Reactor temperature was changed assuming a 2° F. (1° C.) change in product pour point per 1° F. (0.5° C.) change in reactor temperature. Material balance closures were generally at least 95% and results have been nrmalised to a no-loss basis. The run was arbitrarily terminated after 35 days on stream.

The results are given in Table 2 below which gives the lined-out performance of the catalysts for 50° F. (10° C.) and 20° F. (−7° C.) pour points.

TABLE 2

| Dewaxing Catalyst Performance Comparison | | | | |
|---|---|---|---|---|
| Catalyst Characteristics | Pt/HTC ZSM-11 | | Pt/Steamed ZSM-11 | |
| wt. % Pt | 1.2 | | 1.15 | |
| 330° F.+ Pour Point, °F. | 45 | 20 | 50 | 22 |
| Reactor Temperature °F. | 664 | 677 | 710 | 730 |
| Net 650° F.+ Conversion wt. % | 39.7 | 42.7 | 38.9 | 43.9 |
| C4−, wt. % | 5.8 | 7.7 | 2.1 | 4.0 |
| 330° F.+, wt % | 76.0 | 72.9 | 83.0 | 78.1 |
| 650° F.+, wt % | 57.9 | 54.5 | 60.9 | 54.5 |
| 650° F.+ Pour Point, °F. | 65 | | 67 | |
| 650° F.+ Paraffins, wt % | 30.5 | | 37.8 | |
| 650° F.+ Naphthenes, wt % | 42.0 | | 35.0 | |
| 650° F.+ Aromatics, wt % | 27.5 | | 27.2 | |

The reactor temperature during the course of the cycle is shown in the FIGURE for a 50° F. (10° C.) pour point for the 330° F.+ (165° C.+) product.

The FIGURE shows that, although the Pt contents of both catalysts are almost identical, the high temperature calcined version is 40°–50° F. more active than the steamed preparation. The aging rates for both catlysts are comparably low (less than 1° F./day). Inspection of the early on stream time portion of the FIGURE indicated that the calcined catalyst lines out more rapidly than the steamed version. 330° F.+ product yields, for both catalysts increased during the first week on stream, and stabilized after that.

At similar 330° F.+ pour points (45°–50° F.), the 650° F.+ products from both the steamed and calcined versions show comparable pour point reductions vs the 650° F.+ feed (from 115° to about 65° F.). Like 330° F.+ yield, the calcined catalyst's 650° F.+ yield is slightly lower than that of the steamed catalyst and its composition (PNA analysis) reflects somewhat higher paraffin cracking.

We claim:

1. A process for catalytically dewaxing a hydrocarbon feedstock which comprises contacting the feedstock with a solid, porous catalyst comprising a zeolite having a Constraint Index of 1 to 12, a silica:alumina ratio of at least 12:1 and possessing acidic functionality, the zeolite having been heated to a temperature of at least 725° C. in an essentially water-free atmosphere to reduce its acidity to an alpha value below 100.

2. A process according to claim 1 in which the zeolite is heated to a temperature of 725° to 800° C.

3. A process according to claim 1 in which the zeolite is heated to a temperature of at least 800° C.

4. A process according to claim 1 in which the catalyst alpha is less than 50.

5. A process according to claim 1 in which the catalyst alpha is less than 1.

6. A process according to claim 1 in which the heat treatment proceeds for at least one hour.

7. A process according to claim 1 in which the catalyst retains at least 55% of the crystallinity upon heat treatment.

8. A process according to claim 1 in which the heat treatment proceeds in dry air.

9. A process according to claim 1 in which the zeolite is ZSM-5.

10. A process according to claim 1 in which the zeolite is ZSM-11.

11. A process according to claim 1 in which the zeolite is ZSM-23.

12. A process according to claim 1 in which the catalyst includes a hydrogenation-dehydrogenation component.

13. A process according to claim 12 in which the hydrogenation-dehydrogenation component comprises a metal of Group VIIIA.

14. A process according to claim 13 in which the metal of Group VIIIA comprises nickel.

15. A process according to claim 13 in which the metal of Group VIIIA comprises palladium.

16. A process according to claim 13 in which the metal of Group VIIIA comprises platinum.

17. A process according to claim 1 in which the feed is contacted with the catalyst at a temperature of at least 400° F. in the presence of hydrogen.

18. A process according to claim 17 in which the feed is contacted with the catalyst at a temperature from 500° to 800° F. in the presence of hydrogen at a pressure of at least 400 psig.

19. A process according to claim 1 in which the feedstock has a boiling range within the range of 330° to 1050° F.

20. A process according to claim 19 in which the feedstock comprises a middle distillate or a distillate lubricating oil fraction.

* * * * *